(12) United States Patent
Suarez et al.

(10) Patent No.: US 9,996,681 B2
(45) Date of Patent: Jun. 12, 2018

(54) MOBILE DEVICE ACCESS FOR MEDICAL DEVICES

(75) Inventors: David Eduardo Suarez, Escondido, CA (US); Waldemar Roberto Suarez, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 379 days.

(21) Appl. No.: 13/475,895

(22) Filed: May 18, 2012

(65) Prior Publication Data
US 2013/0312066 A1 Nov. 21, 2013

(51) Int. Cl.
  *H04L 29/06* (2006.01)
  *G06F 21/30* (2013.01)
  *G06F 19/00* (2018.01)

(52) U.S. Cl.
  CPC ........ *G06F 21/305* (2013.01); *G06F 19/3406* (2013.01); *G06F 19/3418* (2013.01); *G06F 19/327* (2013.01); *G06F 19/3462* (2013.01); *G06F 19/3468* (2013.01); *G06F 2221/2111* (2013.01)

(58) Field of Classification Search
  CPC ........................ G06F 21/305; G06F 2221/2111
  USPC .......................................................... 726/4
  See application file for complete search history.

(56) References Cited

U.S. PATENT DOCUMENTS

| | | | | |
|---|---|---|---|---|
| 5,960,085 A * | 9/1999 | de la Huerga | ........ | A61J 1/1437 235/380 |
| 6,937,150 B2 * | 8/2005 | Medema | ................ | H04W 64/00 340/286.07 |
| 7,487,233 B2 * | 2/2009 | Iwamoto | ................ | G06F 21/604 709/223 |
| 7,835,927 B2 | 11/2010 | Schlotterbeck et al. | | |
| 8,639,346 B2 * | 1/2014 | Seeberger | .......... | A61N 1/37252 607/59 |
| 2002/0178126 A1 * | 11/2002 | Beck | .................... | A61B 5/0002 705/75 |
| 2003/0040938 A1 | 2/2003 | Ng et al. | | |

(Continued)

FOREIGN PATENT DOCUMENTS

| | | |
|---|---|---|
| CN | 101589393 A | 11/2009 |
| EP | 1750573 A1 | 2/2007 |

(Continued)

OTHER PUBLICATIONS

International Search Report and Written Opinion dated Jul. 16, 2013 for PCT/US2013/037003 in 12 pages.

(Continued)

*Primary Examiner* — Harris C Wang
(74) *Attorney, Agent, or Firm* — McDermott Will & Emery LLP

(57) ABSTRACT

Methods for controlling a medical device using a software application on a mobile device are provided. In one aspect, a method includes receiving a request from the software application on the mobile device to open a communications channel for at least one of audio communication or text-based communication, and sending from the server an instruction to the medical device based on the request. The method also includes providing to the software application on the mobile device for display a result of the instruction. Systems, graphical user interfaces, and machine-readable media are also provided.

31 Claims, 11 Drawing Sheets

(56) References Cited

U.S. PATENT DOCUMENTS

| | | | |
|---|---|---|---|
| 2003/0065536 A1* | 4/2003 | Hansen | A61B 5/14532 |
| | | | 705/2 |
| 2005/0055242 A1* | 3/2005 | Bello | G06Q 50/22 |
| | | | 705/2 |
| 2007/0179815 A1* | 8/2007 | Vining | G06F 19/322 |
| | | | 705/3 |
| 2008/0021834 A1* | 1/2008 | Holla | G06F 19/322 |
| | | | 705/51 |
| 2008/0088436 A1* | 4/2008 | Reeves | A61B 5/0031 |
| | | | 340/539.12 |
| 2008/0091175 A1 | 4/2008 | Frikart et al. | |
| 2008/0319510 A1* | 12/2008 | Simpson | A61N 1/37235 |
| | | | 607/59 |
| 2009/0099867 A1 | 4/2009 | Newman | |
| 2009/0249076 A1* | 10/2009 | Reed | G06Q 30/00 |
| | | | 713/181 |
| 2010/0131294 A1* | 5/2010 | Venon | G06F 19/321 |
| | | | 705/3 |
| 2010/0198608 A1* | 8/2010 | Kaboff | G06Q 10/00 |
| | | | 705/2 |
| 2011/0093283 A1 | 4/2011 | Dicks et al. | |
| 2012/0163663 A1* | 6/2012 | Masoud | A61N 1/37229 |
| | | | 382/103 |
| 2012/0232918 A1* | 9/2012 | Mack | G06F 19/3418 |
| | | | 705/2 |
| 2013/0312066 A1* | 11/2013 | Suarez | G06F 19/3418 |
| | | | 726/4 |

FOREIGN PATENT DOCUMENTS

| | | |
|---|---|---|
| JP | 2007286879 A | 11/2007 |
| JP | 2011523869 A | 8/2011 |
| WO | WO-2008052034 A1 | 5/2008 |
| WO | WO-2012061825 A2 | 5/2012 |

OTHER PUBLICATIONS

Chinese Office Action for Application No. 201380032595.2, dated Feb. 16, 2017, 8 pages excluding translation.
English language memo of Mexican Office Action for Application No. MX/a/2014/013952, dated Mar. 11, 2016, 5 pages.
Extended European Search Report for Application No. 13790344.9, dated Jan. 14, 2016, 8 pages.
English language Memo of Mexican Office Action for Application No. MX/a/2014/013952, dated Dec. 7, 2015, 2 pages.
Australian Examination Report No. 1 for Application No. 2013263308, dated Aug. 30, 2017, 3 pages.
Chinese Office Action for Application No. 201380032595.2, dated Sep. 27, 2017, 6 pages excluding English translation.
European Office Action for Application No. 13790344.9, dated Feb. 8, 2018, 7 pages.

* cited by examiner

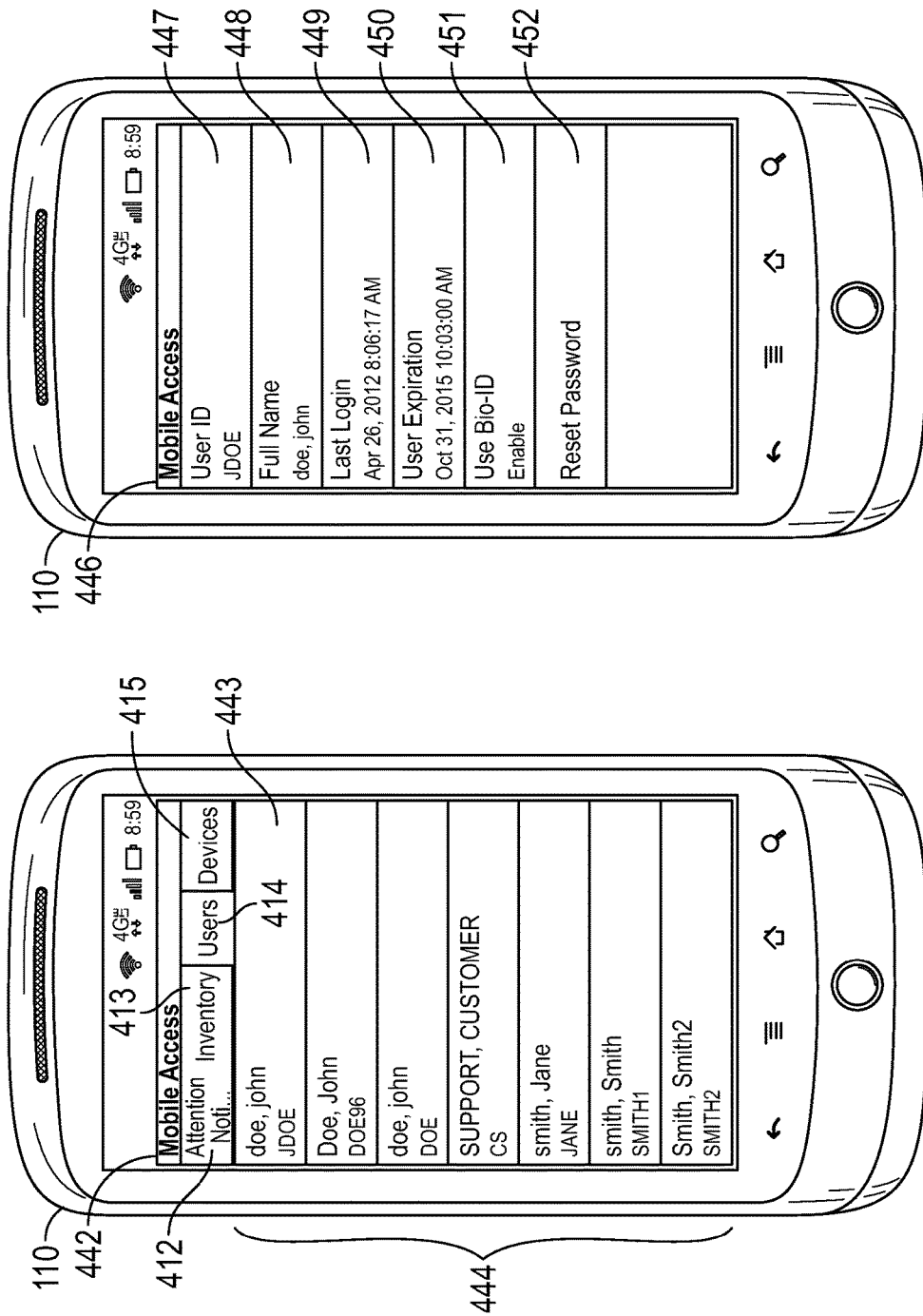

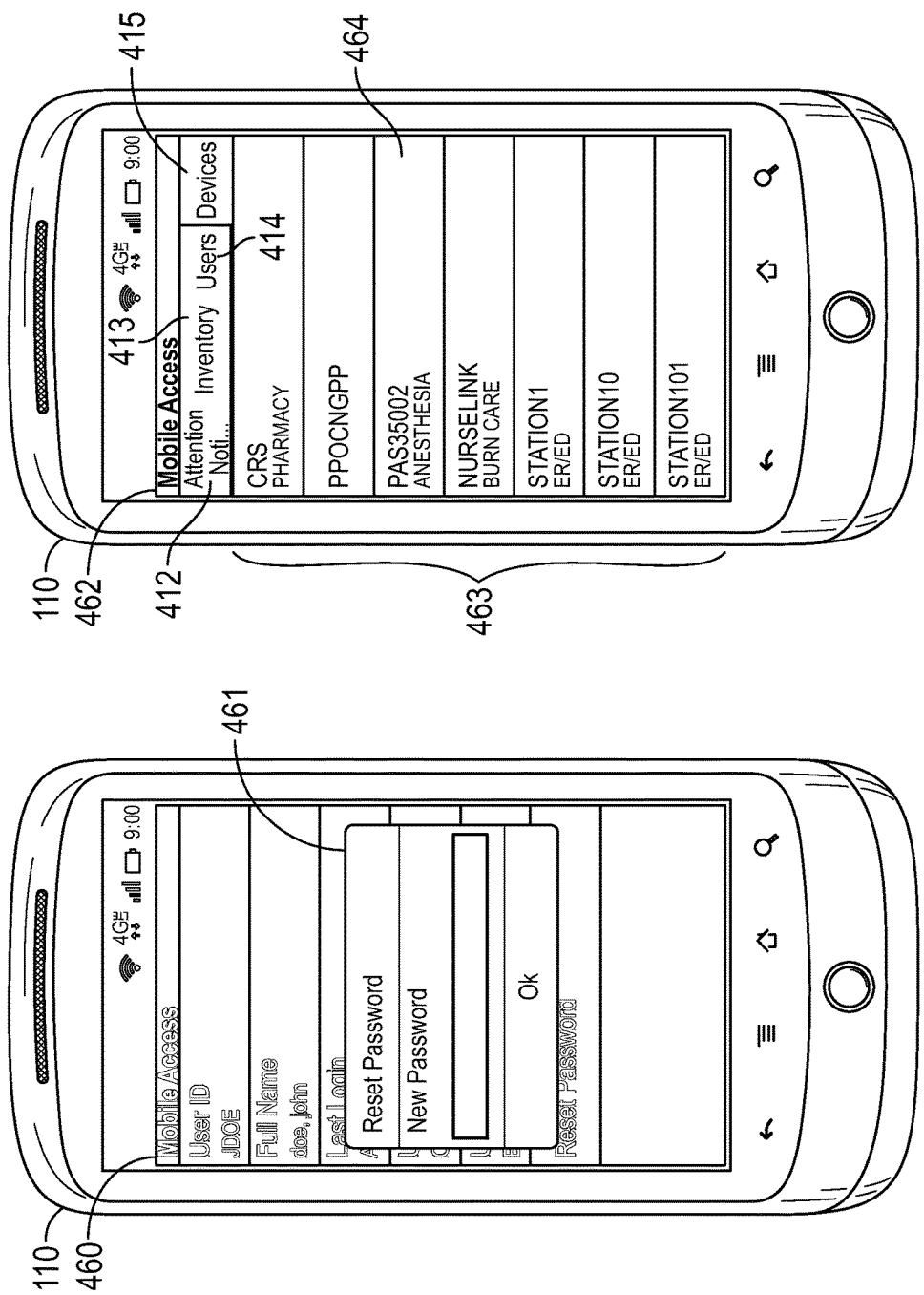

MOBILE DEVICE ACCESS FOR MEDICAL DEVICES

BACKGROUND

Field

The present disclosure generally relates to providing health care using medical devices, and in particular, relates to controlling access to medical devices.

Description of the Related Art

Access to a medical device, such as an infusion system, dispensing machine, respirator, or vital sign monitor, is commonly restricted due to concerns regarding the health of one or many patients affected by the medical device. For example, a dispensing machine that tracks and dispenses medical products such as medications, medical devices, etc., often includes access restrictions so that its medical products can be tracked, and theft or misuse can be prevented. As another example, an infusion pump that delivers medication in a controlled manner to a patient often includes restrictions that permit only authorized users to configure the infusion pump.

The ability for certain authorized users, such as pharmacists, pharmacy technicians, and system administrators, to access and configure such medical devices is commonly restricted to one or many physical locations. For example, a medical device can be located at a first physical location and permit an authorized medical device user such as a nurse to access the device. At a second physical location apart from the first physical location, a server can be present that permits an authorized server user, such as a pharmacist or a system administrator, to access and configure the nurse's access to the medical device. As a result, if the pharmacist or system administrator wants to change the nurse's access to the medical device or change a configuration of the medical device, the pharmacist or system administrator must be present at the physical location of the server in order to do so.

SUMMARY

Embodiments described herein address the foregoing problems by providing an interface on a mobile device that permits an authorized user to access and configure a medical device from any location. For example, using a software application on a smartphone or tablet computer, an authorized pharmacist can, for example, from anywhere adjust another user's access to a medical device, obtain current information on the medical device, or change the way the medical device operates using a server connected to the mobile device and the medical device. For instance, the authorized pharmacist can modify a nurse's password or permission to access the medical device. The authorized pharmacist can be located anywhere that the pharmacist's mobile device has access to a network that is connected to the server and the medical device. Using the mobile device, the authorized pharmacist is no longer required to be in any certain physical location in order to access or configure a medical device.

According to one embodiment of the present disclosure, a system for controlling a medical device using a software application on a mobile device is provided. The system includes a memory that includes instructions, and a processor. The processor is configured to execute the instructions to receive a request from the software application on the mobile device to open a communications channel for at least one of audio communication or text-based communication, and send an instruction from the server to the medical device based on the request. The processor is also configured to execute the instructions to provide to the software application on the mobile device for display a result of the instruction.

According to one embodiment of the present disclosure, a method for controlling a medical device using a software application on a mobile device is provided. The method includes receiving a request from the software application on the mobile device to open a communications channel for at least one of audio communication or text-based communication, and sending from the server an instruction to the medical device based on the request. The method also includes providing to the software application on the mobile device for display a result of the instruction.

According to one embodiment of the present disclosure, a machine-readable storage medium that is provided includes machine-readable instructions for causing a processor to execute a method for controlling a medical device using a software application on a mobile device. The method includes receiving a request from the software application on the mobile device to open a communications channel for at least one of audio communication or text-based communication, and sending from the server an instruction to the medical device based on the request. The method also includes providing to the software application on the mobile device for display a result of the instruction.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

In the following detailed description, numerous specific details are set forth to provide a full understanding of the present disclosure. It will be apparent, however, to one ordinarily skilled in the art that the embodiments of the present disclosure may be practiced without some of these specific details. In other instances, well-known structures and techniques have not been shown in detail so as not to obscure the disclosure.

Figure 1:
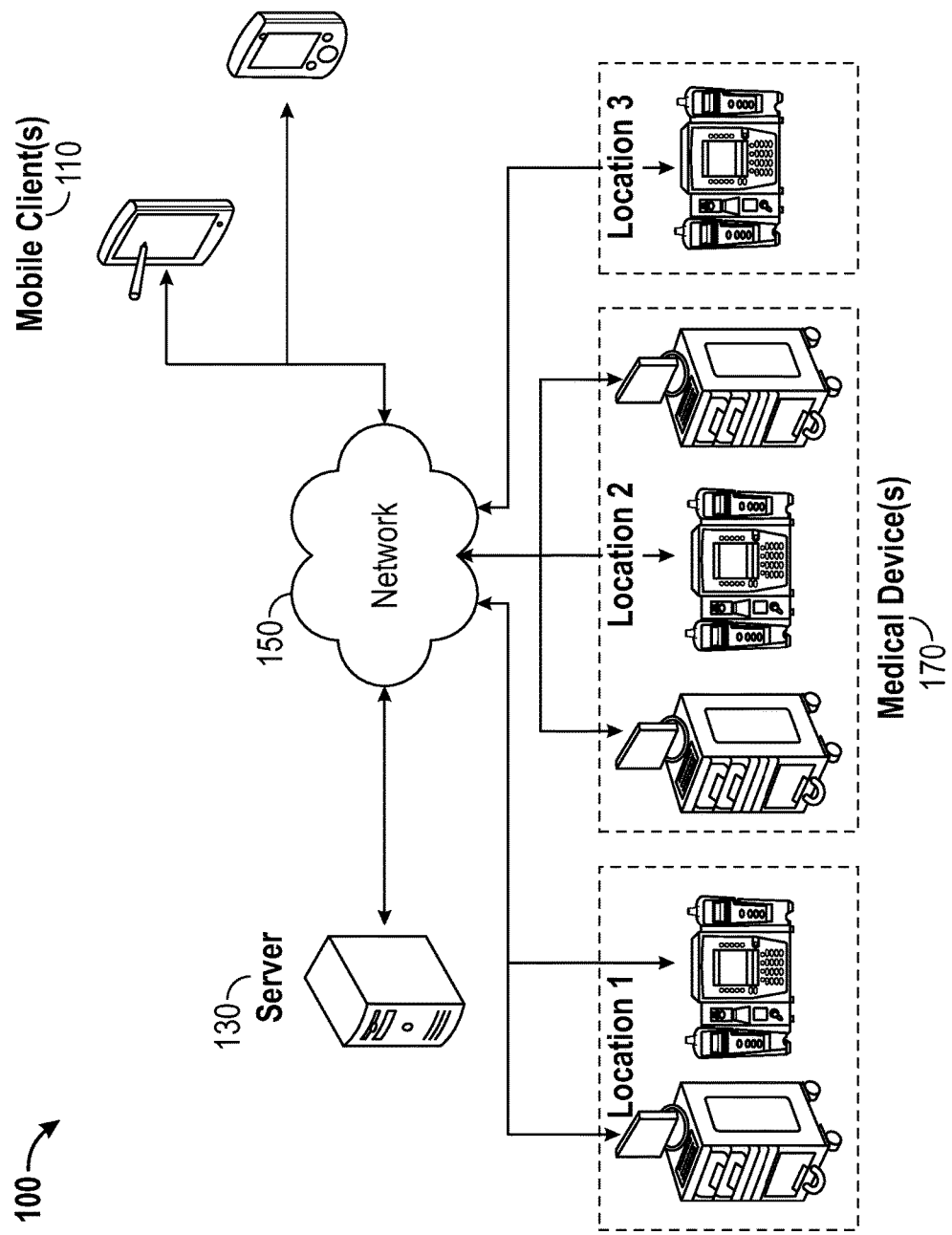
FIG. 1 illustrates an example architecture for controlling one or many medical devices from a software application on a mobile device.

Referring now to the drawings, FIG. 1 illustrates an example architecture 100 for controlling one or many medical devices 170 in different locations using a software application on a mobile client 110. The architecture 100 includes a server 130, mobile client(s) 110, and medical device(s) 170 in different locations connected over a network 150. The network 150 can include, for example, any one or more of a personal area network (PAN), a local area network (LAN), a campus area network (CAN), a metropolitan area network (MAN), a wide area network (WAN), a broadband network (BBN), the Internet, and the like. Further, the network 150 can include, but is not limited to, any one or more of the following network topologies, including a bus network, a star network, a ring network, a mesh network, a star-bus network, tree or hierarchical network, and the like.

The server 130 is configured to host a service for communicating with the mobile clients 110 and the medical devices 170. The server 130 is commonly a large, non-mobile (e.g., fixed) computing device located in a pharmacy or another restricted access area of a healthcare institution. The server 130 can be any device having an appropriate processor, memory, and communications capability for hosting a service. Using the service, the server 130 is configured to permit authorized users of the mobile clients 110 ("authorized mobile client users"), such as pharmacists, pharmacy technicians, materials management employees, pharmacy staff, and system administrators, to access and configure the medical devices 170 over the network 150 without requiring these authorized mobile client users to be present at either the location of the server 130 or the locations of the medical devices 170. Similarly, using the service, the server 130 is configured to restrict authorized users ("authorized medical device users") limited to accessing the medical devices 170 but not having authorization to access the server 170, such as nurses, from accessing and configuring the medical devices 170 over the network 150. In certain aspects, authorized mobile client users have the medical device 170 access privileges of authorized medical device users, but authorized medical device users do not have the medical device 170, server 130, and mobile client 110 access privileges of authorized mobile client users. In certain aspects, the server 130 has an interface for accessing and configuring the medical devices 170 over the network 150 that includes a subset of the configurable features for one or many of the medical devices 170. The interface on the server 130 can, for example, communicate with an Internet information server or other web server in order to communicate with the medical devices 170. Such an interface, however, is not configured for use with a mobile client 110.

The disclosed service on the server 130, however, can be configured to communicate with the interface (e.g., using an application programming interface) on the server 130 in order to access the medical devices 170. Using a software application on the mobile client 110 that is configured to connect to the service on the server 130, an authorized mobile client user can, for example, configure one, many, or all of the medical devices 170 and receive information on medical devices 170. As a result, the authorized mobile client user no longer needs to be physically present at the server 130 or the medical devices 170 in order to configure the medical devices 170.

The mobile client 110 is configured to connect to the service on the server 170. The mobile client 110 can be, for example, a tablet computer (e.g., including an e-book reader), mobile telephone (e.g., a smartphone), mobile organizer (e.g., a personal digital assistant), or any other mobile device having appropriate processor, memory, and communications capabilities. Using an interface specifically designated for the mobile client 110, an authorized mobile client user can communicate with the service running on the server 130 in order to access and/or configure one, many, or all of the medical devices 170 over the network 150. The interface can be, for example, a mobile software application that can be downloaded from the server 170 or another server, or a World Wide Web (e.g., HyperText Markup Language) page interface accessible from a mobile web browser on the mobile client 110.

The medical devices 170 are connected over the network 150 to the server 130, and are commonly referred to as connected devices. The medical devices 170 can be, for example, connected health care technologies such as intravenous (or "infusion") pumps, automated dispensing machines, patient identification systems, ventilators and respiratory products, skin preparation products, infection surveillance devices, surgical instruments, monitoring equipment, and diagnostic products. Although infusion pumps and automated dispensing machines are referred to in the examples described herein, any other connected medical device 170 having an appropriate processor, memory, and communications capabilities for connecting to the mobile client 110 or server 130 over the network 150 can be used. The medical devices 170 can be located in a single physical location or across multiple physical locations spread throughout a geographic region. For example, a first location in Central City for Central City Hospital can include an automated dispensing machine 170 and infusion pump 170 in Building A, which is located in a northern region of Central City. A second location in Central City for Central City Hospital can include two automated dispensing machines 170 and an infusion pump 170 in Building B, located in a southern region of Central City five miles away from Building A. A third location in Central City for Central City Hospital can include an infusion pump 170 in Building C, located in a western region of Central City ten miles away from both Building A and Building B. The medical devices 170 of Buildings A, B, and C, however, are each connected to the network 150 and are part of the same medical group. As a result, each of the infusion pumps 170 and automated dispensing machines 170 in any of the three different locations in Central City can be controlled by an authorized mobile client user from the mobile client 110 over the network 150.

In certain aspects, an authorized mobile client user can nonetheless be restricted from accessing and configuring a medical device 170 if the authorized mobile client user is not within a pre-determined range of the medical device 170 and/or the server 130. The authorized mobile client user's location can be determined using a location sensor present in the mobile client 110, such as a Global Positioning System (GPS) sensor or by network triangulation. For example, if the authorized mobile client user is more than one mile away from a medical device 170 or an institution where the medical device 170 is located, then the authorized mobile client user may not be given access to the medical device 170 even though the user inputs appropriate authentication to access the medical device 170. In such instances, a notification may be displayed on the mobile client 110 that indicates the user is out of range to access the medical device 170. Similarly, an authorized mobile client user can be provided physical access to a medical device 170 if the authorized mobile client user is within a pre-determined range of the medical device 170. For example, if the authorized mobile client user is less than 10 feet away from an automated dispensing machine 170, then the user upon providing appropriate authorization to the mobile client 110 may be given access to control the automated dispensing machine 170.

In certain aspects, each medical device 170 has an interface at the medical device 170 itself for accessing and configuring the medical device 170. The interface at the medical device 170 may include a subset of the configurable features for the medical device 170. The interface of the medical device 170 is not configured for use with a mobile client 110. The interface at the medical device 170 is commonly accessed by authorized medical device users that do not otherwise have authorization to access to the server 130, and therefore would not be permitted to use a mobile client 110 to access the service on the server 130. The interface at the medical device 170 can also be accessed by authorized mobile client users such as pharmacists and pharmacy technicians that do have access to the server 130, and therefore would be permitted to use a mobile client 110 to access the service on the server 130. Using a software application on the mobile client 110, an authorized mobile client user can access the interface on the medical device 170 either through the service on the server 130, or by directly connecting to the medical device 170 (e.g., and bypassing the server 130) over the network 150 in order to control or configure the medical device 170 using the subset of configurable features. As a result, the authorized mobile client user no longer needs to be physically present at the medical device 170 or server 130 in order to access or configure the medical device 170.

Figure 2:
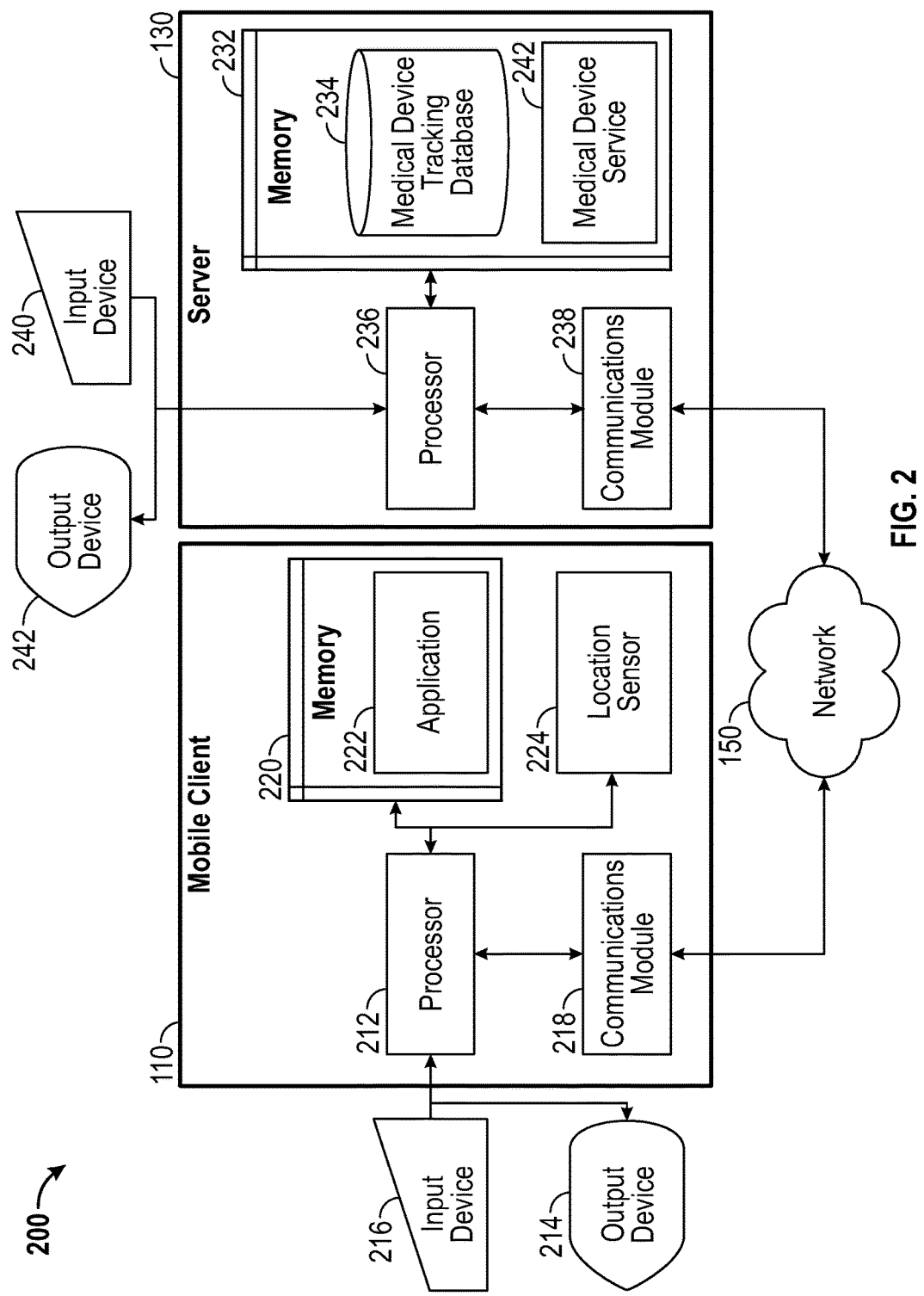
FIG. 2 is a block diagram illustrating an example mobile client and server from the architecture of FIG. 1 according to certain aspects of the disclosure.

FIG. 2 is a block diagram 200 illustrating an example server 130 and client 110 in the architecture 100 of FIG. 1 according to certain aspects of the disclosure. The illustrated configuration is exemplary only, such that other network and device configurations may be employed.

The client 110 and the server 130 are connected over the network 150 via respective communications modules 218 and 238. The communications modules 218 and 238 are configured to interface with the network 150 to send and receive information, such as data, requests, responses, and commands to other devices on the network 150, such as a medical device 170. The communications modules 218 and 238 can be, for example, modems or Ethernet cards.

The server 130 includes a processor 236, a communications module 238, and a memory 232 that includes a medical device service 242 and a medical device tracking database 234. The medical device service 242 is configured to receive and respond to queries generated from an application 222 in a memory 220 of the mobile client 110, and sent to the server 130 by a processor 212 of the mobile client 110 over the network 150 using the communications module 218 of the mobile client 110. The query can be for changing another user's access to a medical device 170, obtaining a current status of the medical device 170, or configuring the medical device 170. The query can be generated by an authorized user of the mobile client 110 and input using an input device 216, such as a touchscreen interface or a physical button, or generated by the application 222 automatically in response to a prior configuration or instruction from an authorized mobile client user.

The medical device service 242 is further configured to provide instructions to one or many medical devices 170 connected to the network 170, such as instructions based on the query from the mobile client 110. The instructions from the medical device service 242 can be communicated to an interface of the medical device 170 for accessing or controlling the medical device 170. The interface can be present on the server 130, the medical device 170, or both the server 130 and the medical device 170. In certain aspects, the medical device service 242 is also configured to provide instructions to the medical device 170 using a different interface designated for mobile client 110 communications, thereby permitting access to the medical device 170 from the application 222 on the mobile client 110.

The medical device tracking database 234 is configured to store information on one or many medical devices 170, such as current inventory information, authorized user information, authorization process information, profile information, and status information. In certain aspects, the medical device tracking database 234 is a database in the memory 232 of the server 130 that is continuously updated by each medical device 170 and/or by an authorized user using an appropriate input device 240 and output device 242 connected to the server 130. Additionally, the medical device tracking database 234 can serve as a repository for storage of data from each of the medical devices 170, thereby serving as a data backup for each medical device 170 and as a second point of information access for each medical device 170.

Turning to the processor 236 of the server 130, the processor 236 is configured to execute instructions, such as instructions physically coded into the processor 236, instructions received from software in memory 240 (e.g., medical device service 242), or a combination of both. For example, the processor 236 of the server 130 executes instructions to receive a request from the application 222 on the mobile client 110 to query a medical device 170. The request the application 222 can be for changing another user's access to a medical device 170, obtaining a current status of the medical device 170, or configuring the medical device 170. Additionally, the request from the application 222 can be for querying a single medical device 170 in a single physical location, multiple medical devices 170 in a single physical location, or multiple medical devices 170 across multiple physical locations. For example, from the application 222 on the mobile client 110, an authorized mobile client user can request a list of current alert notifications for each medical device 170 in four different locations in a hospital. In certain aspects, the alert notifications can be provided to the mobile client 110 using a push notification interface or other interface by which an alert notification can quickly be brought to the attention of the authorized mobile client user.

The processor 236 of the server 130 also executes instructions to send, based on the query, an instruction to the medical device(s) 170 identified by the query, and provide to the application 222 on the mobile client 110 for display (e.g., on output device 214 of the mobile client 110, such as an electronic display) a result of the instruction. For example, the result provided for display on the mobile client 110 can be a confirmation that both the query was received by the medical device service 242 and the instruction was sent to the medical device 170, or the result can be based on an outcome of the instruction sent to the medical device 170 from the server 130. In such instances, the processor 236 of the server 130 is configured to receive from the medical device 170 an outcome of the instruction that can be used for generating the result sent to the mobile client 110. The result that is displayed on the output device 214 of the mobile client 110 can be, for example, current information on the medical device 170, a confirmation that a change has been made to the way the medical device 170 operates, or confirmation that access to the medical device 170 has been changed or remains the same.

In certain aspects, if the medical device tracking database 234 includes information sufficient to respond to the query from the mobile client 110 without contacting the medical device 170, then the processor 236 of the server 130 is configured to provide the information responsive to the query to the mobile client 110 without communicating with the medical device 170. For example, an authorized mobile client user may activate an interface of the application 222 on the mobile client 110 that requests and displays a listing of all medical devices 170 that the authorized mobile client user can access or configure. The medical device service 242 may obtain this information from the medical device tracking database 234 and send the information back to the mobile client 110 for display.

In certain aspects, the processor 236 of the server 130 executes instructions to update the medical device tracking database 234 based on the query, the outcome of the query, or both. For example, if the medical device tracking database 234 indicates that a certain medical device 170 is enabled, and the query from the mobile client 110 is a request by an authorized mobile client user to disable the medical device 170, then the medical device tracking database 234 can be updated to indicate that a request to disable the medical device 170 has been made, and/or indicate that the medical device 170 has been confirmed as disabled.

In many instances, a user must have appropriate authorization to access the application 222 on a mobile client 110 in order to provide queries to a medical device 170. The authorization for a user may be the same as the user's authorization for the server 130 or the medical device 170. The authorization for a user can include a username, password, biometric identifier (e.g., fingerprint or facial scan), associated access privileges, and a time limit for expiration of the access privileges. As such, before a user of the mobile client 110 is given access to configure a medical device 170, the mobile client user must request appropriate authorization from the server 130 for the application 222 running on the mobile client 110. The processor 236 of the server 130 is thus configured to receive a request from the application 122 on the mobile client 110 for authorization to instruct the medical device 170. The request for authorization includes user identification data, such as a username, password, and/or biometric identification. The request for authorization can also include location information for the mobile client 110 that is obtained from a location sensor 224 on the mobile client 110, such as a GPS sensor, Radio Frequency Identification (RFID) sensor, Near Field Communications (NFC) sensor, or by triangulation using a network signal, such as a broadband, WiFi, or Bluetooth network. The processor 236 of the server 130 is also configured to determine whether to authorize the application 222 on the mobile client 110 based on the user identification data, and send an authorization outcome to the application 222 on the mobile client 110 based on the determination.

If mobile client location data is included with the authorization request by the mobile client 110, then the processor 236 of the server 130 is configured to also determine whether to authorize the mobile client 110 based on a proximity of the mobile client location to a location of the medical device 170 or the server 130. For example, if an authorized mobile client user provides an authenticated username and biometric identification to the application 222 on the user's mobile client 110, the server 130 may still reject authorization of the application 222 because the user is too far away from the closest medical device 170 to which access is sought by the mobile client user. This distance is configurable to allow, for example, an authorized mobile client user to make changes within a building or its immediate vicinity, such as a campus, city, or even state. Alternatively, a proximity requirement can be disabled, allowing an authorized mobile client user to interact with the server 130 from anywhere network 150 access is available.

The query for the medical device 170 received by the server 130 from the mobile client 110 can include a request for notifications specific to the medical device 170. For example, an authorized mobile client user may activate an interface of the application 222 on the mobile client 110 that requests and displays current alerts and messages for each medical device 170 that the authorized mobile client user can access or configure.

The query for the medical device 170 received by the server 130 from the mobile client 110 can also include a request for a current status of the medical device 170. The current status of the medical device 170 can, for example, indicate an inventory of the medical device 170, or information indicative of an infusion status of the medical device 170. As one example, an authorized mobile client user may activate an interface of the application 222 on the mobile client 110 that requests and displays a current inventory and configuration for an automated dispensing machine 170.

The query for the medical device 170 received by the server 130 from the mobile client 110 can also include a request to change, for example, information indicative of an inventory of the medical device 170, or to change information indicative of an infusion configuration of the medical device 170. The request to change the information indicative of an inventory of the medical device 170 can include a confirmation that a medical item has been added or removed from the medical device 170. For example, an authorized mobile client user may activate an interface of the application 222 on the mobile client 110 that permits the authorized mobile client user to indicate that the authorized mobile client user or a medical device user has added fifty doses of medication A to an automated dispensing machine 170. Similarly, an authorized mobile client user may activate an interface of the application 222 on the mobile client 110 that permits the user to change an infusion profile of an infusion device 170 from a profile configured for neo-natal use to a profile configured for operating room use.

The query for the medical device 170 received by the server 130 from the mobile client 110 can yet further include a request for a current authorized user list for the medical device 170. For example, an authorized mobile client user may activate using a touchscreen 216 an interface of the application 222 on the mobile client 110 that requests and displays to output device 214 on the mobile client 110 a list of authorized medical device users across many medical devices 170 to which the authorized mobile client user has access. The query for the medical device 170 can also include a request to configure an authorized user account of the medical device 170, such as the account of another authorized mobile client user or the account of an authorized medical device user. For example, an authorized mobile client user such as a system administrator may activate an interface of the application 222 on the mobile client 110 that permits the systems administrator to change the user identification, password, and activation status of nurse accounts for certain medical devices 170.

The query for the medical device 170 received by the server 130 from the mobile client 110 can also include a request for a name of the medical device 170, a request for a location of the medical device 170, a request to configure an authorization process for the medical device 170, and/or a request to configure an availability of the medical device 170. For example, an authorized mobile client user may activate an interface of the application 222 on the mobile client 110 that requests and displays a list of medical devices 170 to which the user has access. Each medical device 170 can be listed by name and ordered by proximity to the authorized mobile client user. The user can then select a medical device 170 from the list in order to change the authorization process (e.g., from requiring a password to requiring biometric identification) or availability (e.g., whether the medical device 170 is active) of the selected medical device 170.

In certain aspects, an authorized mobile client user may desire to communicate directly with another user at the server 130. This is often the case where, for example, the other user at the server 130 does not have telephone access. The authorized mobile client user may then use the application 222 on the mobile client 110 to communicate over the network 150 by voice or text-based messaging with the other user at the server 130. In such instances, the processor 236 of the server 130 is configured to execute instructions to receive a request from the application 222 on the mobile client 110 to open a communications channel for at least one of audio communication or text-based communication, open the communications channel, and send information on the open communications channel to the application 222 on the mobile client 110. The authorized mobile client user can then either talk or message the user at the server 130 using their corresponding input devices 216 and 240 and output devices 214 and 242.

Although the medical device service 242 is illustrated in FIG. 2 as being in the same memory 232 as the medical device tracking database 234 of a single server 130, the medical device tracking database 234 can instead be located in a memory of a different server connected to the network 150. The medical device service 242 may then access the medical device tracking database 234 on the other server over the network 150 while the medical device service 242 runs on a server 130 specifically designated for the medical device service 242.

Figure 3:
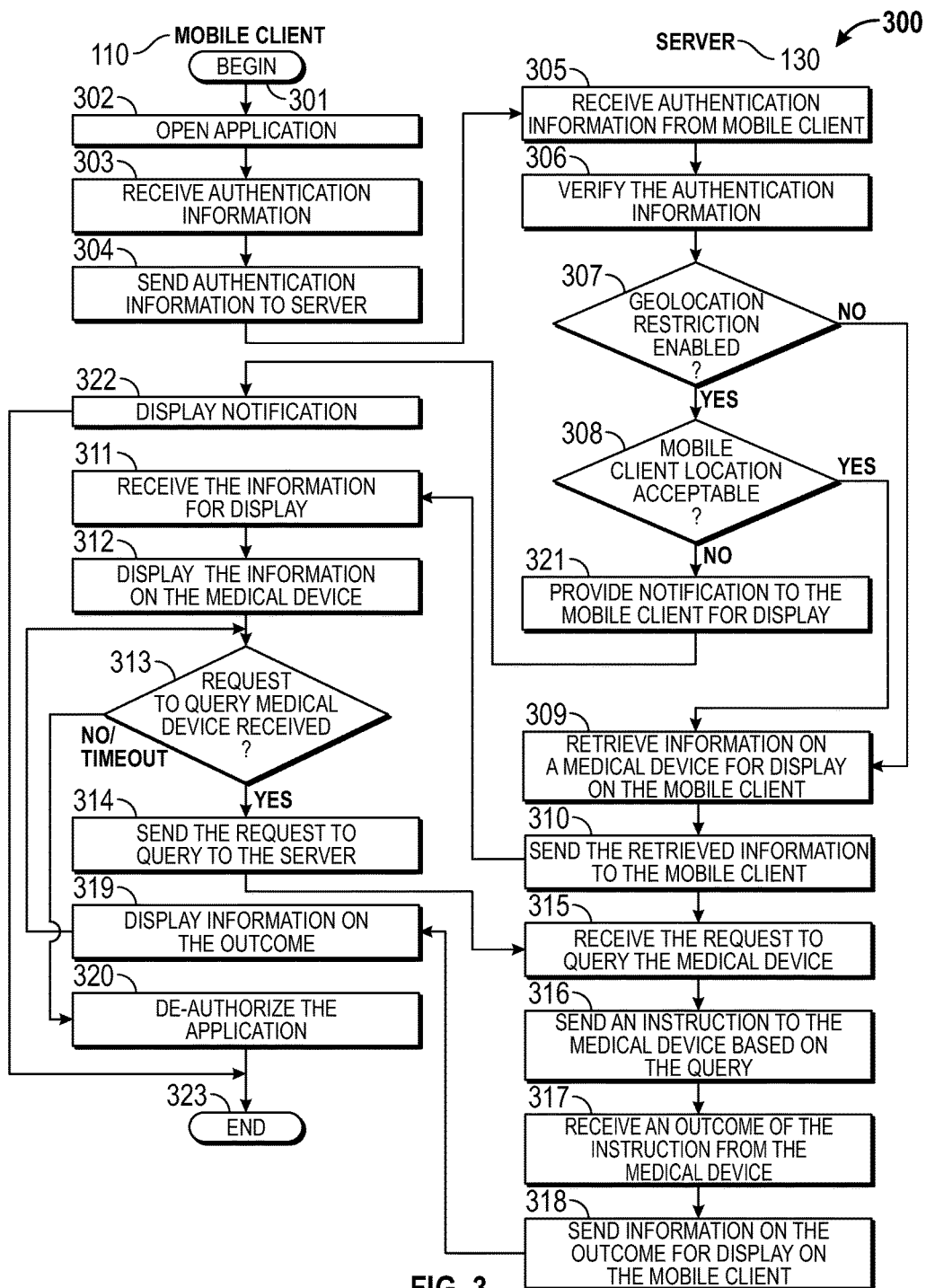
FIG. 3 illustrates an example process for controlling one or many medical devices using the example client and server of FIG. 2.

FIG. 3 illustrates an example process 300 for controlling a medical device 170 using a software application 222 on a mobile device 110 using the example mobile client 110 and server 130 of FIG. 2. While FIG. 3 is described with reference to FIG. 2, it should be noted that the process steps of FIG. 3 may be performed by other systems. The process 300 begins by proceeding from beginning step 301 to step 302 when the application 222 on the mobile client 110 is launched, switched to, or otherwise opened. Next, in step 303, authentication information for a mobile client user is received by the mobile client 110, which can include a geolocation of the mobile client from the location sensor 224, and the authentication information is sent from the mobile client 110 to the server 130 over the network 150 in step 304.

Turning to the server 130, in step 305 of the process 300 the server 130 receives the authentication information from the mobile client 110 and verifies the authentication information in step 306. If a determination is made in step 307 that geolocation restriction for authorized mobile client users has been enabled, then the process 300 proceeds to decision step 308, otherwise the process 300 proceeds to step 309.

In decision step 308, a determination is made whether the mobile client 110 is in an acceptable geolocation based on the geolocation provided by the mobile client as part of the authentication information. If the mobile client 110 is an acceptable geolocation, such as within a certain range of a medical device 170 or an institution associated with the authorized mobile client user responsible for a medical device 170, then the process 300 proceeds to step 309. If, however, the mobile client 110 is not in an acceptable geolocation, or if the mobile client 110 has not provided geolocation information, then the process 300 proceeds to step 321. In step 321, a notification is provided for display on the mobile client 110, and the notification is displayed on the mobile client 110 in step 322. The notification can indicate to the authorized mobile client user, for example, that the authorized mobile client user is too far away from the institution or the medical device 170. The process 300 then ends in step 323.

In step 309, information regarding a medical device 170 selected by an authorized mobile client user is retrieved for display on the mobile client 110, and the retrieved information is sent to the mobile client 110 in step 310 for the mobile client 110 to display.

In step 311, the mobile client 110 receives the information for display from the server 130, and in step 312 the mobile client 110 displays the information on the output device 214 of the mobile client 110. In decision step 313, a determination is made on the mobile client 110 about whether a request to query a medical device 170 has been received. If a request to query a medical device 170 is received, such as a request to configure the medical device 170, control a user account for the medical device 170, or obtain a current status of the medical device 170, then the request is sent by the mobile client 110 to the server 130 in step 314.

Turning back to the server 130, in step 315 the request to query the medical device 170 is received from the mobile client 110, and an appropriate instruction based on the query is sent by the medical device service 242 to the medical device 170, if needed, in step 316. The instruction can be sent by the medical device service 242 using an interface on the server 130 that is instructed according to the request to query from the mobile client 110. In certain aspects, the medical device service 242 can bypass the interface on the server 130 and instead send an instruction directly to the medical device 170 over the network 150. In step 317, an outcome of the instruction sent to the medical device 170 in step 316 is received by the server 130, and in step 318 information on the outcome is provided by the server 130 to the mobile client 110 for display.

The mobile client 110 in step 319 displays the information provided on the outcome of the instruction sent to the medical device 170. By advantageously limiting content for display by the application 222 on the mobile client 110 to information that is provided by the server 130, the mobile client 110 does not store or otherwise retain any information on the medical device 170 that is received from the server 130. Instead, the mobile client 110 simply displays information based on what is provided from the server 130 and limits usage of the memory 220 on the mobile client 110 to storage of the application 222. Restricting memory 220 storage on the mobile client 110 to storage of the application 222 reduces the likelihood that information compromising patient and/or health care institutional privacy can be retrieved from the memory 220 of the mobile client 110 by an unauthorized user.

After step 319, the process 300 returns to decision step 313 to wait for another request to query a medical device 170. If a request to query a medical device 170 is not received in decision step 313, such as within a certain pre-determined timeout period, then the process 300 proceeds to step 318 in which the application 222 is de-authorized, thereby restricting access from the mobile client 110 to the medical devices 170. The process 300 then ends in step 323.

FIG. 3 set forth an example process 300 for controlling a medical device 170 using a software application 222 on a mobile device with the example mobile client 110 and server 130 of FIG. 2. An example will now be described using the example process 300 of FIG. 3, an authorized mobile client user that is a pharmacist, a mobile client 110 that is a touchscreen-enabled smartphone, and several medical devices 170 that are automated dispensing machines controlling access to medications.

The process 300 begins by proceeding from beginning step 301 to step 302 when a pharmacist launches the application 222 on the pharmacist's smartphone 110. In response, the application 222 displays an authentication interface 408 as provided in the example illustration of FIG. 4A. The authentication interface 408 includes fields for a user identification 402 and password 404, and a button 406 to submit for authentication the provided user identification and password. Next, in step 303, the pharmacist enters the pharmacist's user identification and password into the appropriate fields 402 and 404 and presses the login button 406. The provided authentication information is sent from the smartphone 110 to the server 130 over the network 150 in step 304, along with information on a current geolocation of the smartphone 110 obtained from a GPS sensor 224 in the smartphone 110.

Turning to the server 130, in step 305 the medical device service 242 receives the authentication information from the smartphone 110 and verifies that the authentication information provided by the pharmacist in step 306 is correct. The pharmacist's user identification and password is properly verified. The server 130 then determines in decision step 307 that geolocation restriction has been enabled, so the server in decision step 308 determines whether the smartphone 110 is in an acceptable geolocation based on the geolocation information provided by the smartphone 110. The server 110 determines in decision step 308 that the smartphone 110 is in an acceptable location, namely, within one mile of the closest associated medical device 170 that the pharmacist has access to configure, so the process proceeds to step 309. In step 309, the medical device service 242 retrieves, in accordance with the pharmacist's configured preferences, current attention notices for each automated dispensing machine 170 to which the pharmacist has access and can configure. The retrieved notices information is sent to the smartphone 110 in step 310 for the application 222 to display.

Figure 4B:
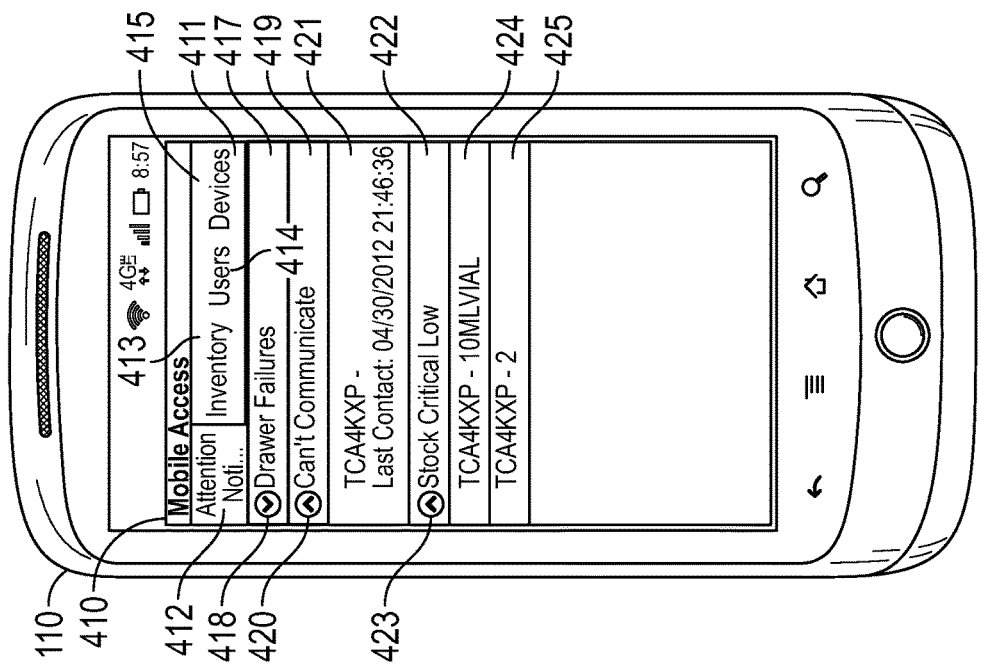
FIGS. 4A-4N are example illustrations of interfaces for controlling one or many medical devices from the software application on the mobile device.
Figure 4A:
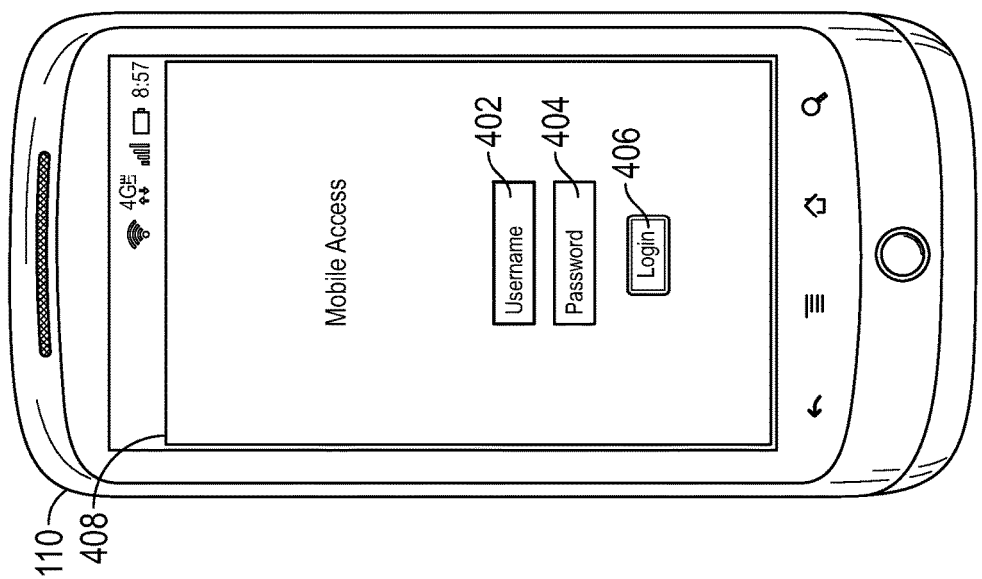

In step 311, the application 222 receives the notices information from the server 130, and in step 312 the application 222 displays the notices information on the touchscreen display of the smartphone 110, as provided in the example notices user interface 410 of FIG. 4B. The notices user interface 410 includes a row 411 of buttons for accessing different information for the automated dispensing machines 170, including a button for displaying attention notices 412, a button for displaying inventory 413, a button for displaying authorized users 414, and a button for displaying accessible devices 415. The button for displaying attention notices 412 may be indicated as being the active interface for the notices user interface 410 using bolding, shading, or other illustrative methods. Each row item 417, 419, 422, 424, and 425 indicates an attention notice or information associated with an attention notice. For example, a first attention notice for drawer failures is displayed 417 with an expand indicator 418 that indicates additional information on the drawer failures will be displayed (e.g., which automated dispensing machines 170 are having drawer failures) if the expand indicator 418 is activated. A second attention notice indicating communication failures 419 is also displayed, although the second attention notice 419 is displayed with a collapse indicator 420 indicating that the information below the second attention notice 419 provides additional information for the second attention notice 419. Specifically, the row 421 below the second attention notice indicating communication failures 419 identifies a specific automated dispensing machine 170 named "TCA4KXP" and the last time of contact with the automated dispensing machine 170. A third attention notice indicating automated dispensing machines having medication stock in a critically low state 422 is also displayed with a collapse indicator 423. Each of the two rows 424 and 425 below the third attention notice 422 indicate that medication stock for "10MLVIAL" and medications in position 2 are critically low for the automated dispensing machine 170 named "TCA4KXP." The displayed notices can be grouped and categorized by severity, and can be displayed with colors matching the severity level identified by the corresponding automated dispensing machine 170.

Returning to decision step 313, the pharmacist presses the button for displaying inventory 413 in the example notices user interface 410, and a determination is made in decision step 313 that a request to query an automated dispensing machine 170, namely for displaying inventory, has been received. The request is sent by the application 222 to the server 130 in step 314.

Turning back to the server 130, in step 315 the request to query the automated dispensing machine 170 for inventory information is received from the mobile client 110, and an appropriate instruction requesting inventory information for each automated dispensing machine 170 the pharmacist has access to and configure is sent to the corresponding automated dispensing machines 170 in step 316. In step 317, each automated dispensing machine 170 provides an updated inventory list to the server 130, and in step 318 the server 130 provides information on the updated inventory lists for the automated dispensing machines 170 to the application 222 for display on the mobile client 110.

Figures 4C, 4D:
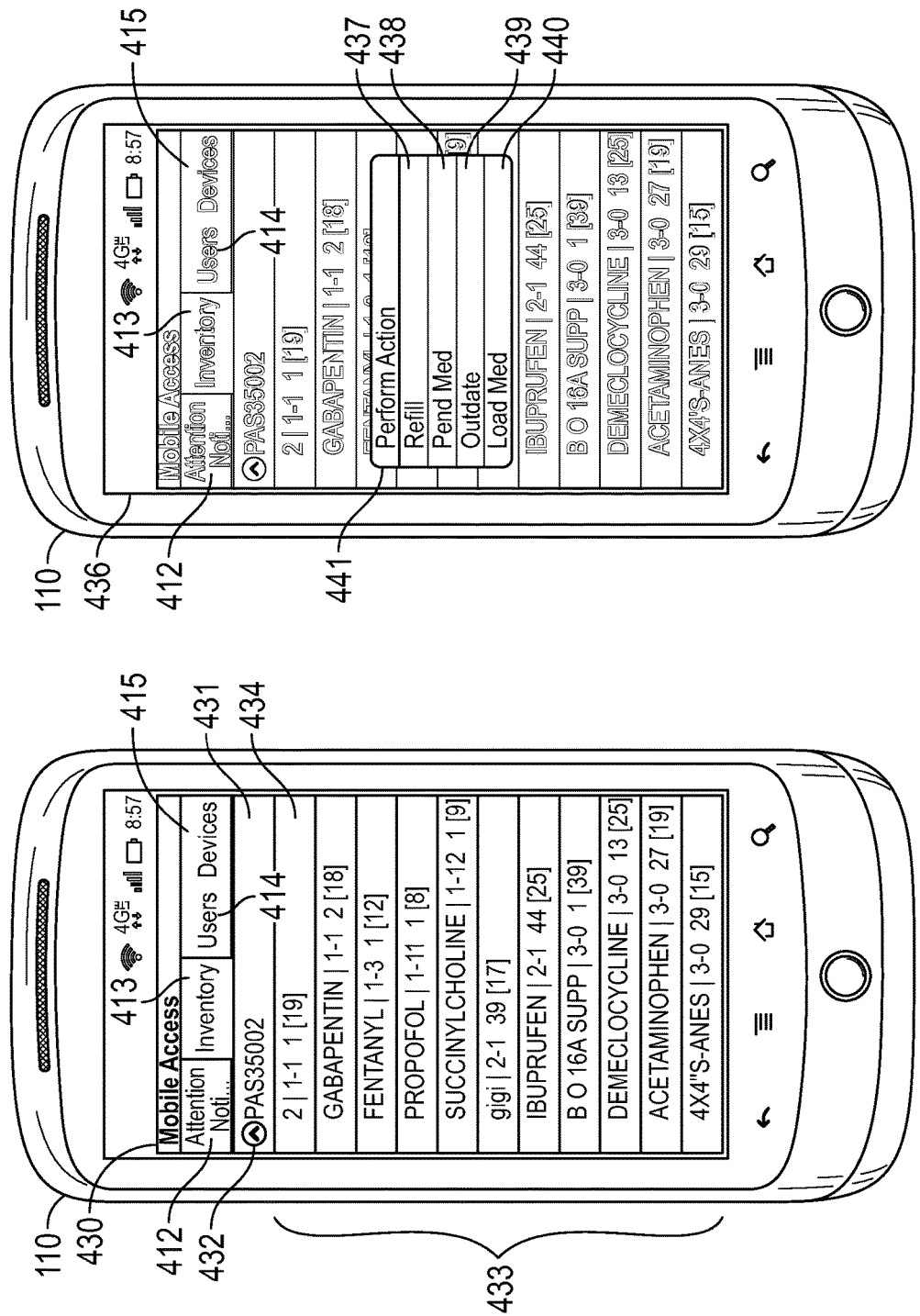

The mobile client in step 319 displays the inventory information for the automated dispensing machines 170 as provided in the example inventory interface 413 of FIG. 4C. The inventory interface 413 lists an automated dispensing machine 170 named "PAS35002" 431 that has the inventory 433 in the locations identified below the identification 431 of the automated dispensing machine 170. For example, the medication "gabapentin" 434 is identified as being "1-1 2 [18]," which indicates that 18 doses of Gabapentin are located in drawer 1, sub-drawer 1, pocket 2 of the automated dispensing machine "PAS35002" 170. A collapse indicator 432 is also displayed with the listing of the automated dispensing machine 170 named "PAS35002" 431, such that if the pharmacist presses the collapse indicator 432, the displayed inventory 433 for automated dispensing machine 170 "PAS35002" will no longer be displayed. Any information below the currently displayed inventory information 433 will be displayed instead.

The process 300 returns to decision step 313 to wait for another request to query an automated dispensing machine 170. The pharmacist using a touch input presses and holds the input on the row 431 for the automated dispensing machine "PAS35002" 170. The application 222 determines that a request to perform an action on the automated dispensing machine "PAS35002" 170 has been received, and the request is sent by the application 222 to the server 130 in step 314. In step 315 the request to perform an action on the automated dispensing machine 170 is received from the smartphone 110, and an appropriate instruction requesting performable actions by the pharmacist for the automated dispensing machine "PAS35002" 170 is sent to the corresponding automated dispensing machine 170 in step 316. In step 317, the automated dispensing machine "PAS35002" 170 provides information on performable actions to the server 130. In step 318, the server 130 provides, to the application 222 for display on the smartphone 110, information on the performable actions for the automated dispensing machine "PAS35002" 170.

The smartphone 110 in step 319 displays a list 441 that includes the performable actions 437, 438, 439, and 440 for the automated dispensing machine "PAS35002" 170 as provided in the example actions interface 441 of FIG. 4D. The actions interface 441 lists four actions that can be executed by the pharmacist using the pharmacist's smartphone 110: refill 437, pend med 438 (e.g., indicating a medication will be filled/re-filled in the automated dispensing machine), outdate 439 (e.g., identify an earliest expiration date of one or many medications in the automated dispensing machine), and load med 440. The pharmacist can select one of the four actions 437, 438, 439, and 440 by touching the action on the touchscreen of the smartphone 110.

For example, the pharmacist can touch the refill 437 action, and a prompt (not illustrated) will be displayed asking the pharmacist to specify the information for a medication refill for the automated dispensing machine 170. As another example, the pharmacist can touch the pend med 438 action, and a prompt (not illustrated) will be displayed asking the pharmacist to specify using the smartphone 110 and when near the automated dispensing machine 170 the information for a medication to be added to the automated dispensing machine 170. Previously, in order to execute a pend med action without a mobile client 110, the pharmacist would have to: (1) receive a request to add medications to an automated dispensing machine 170, (2) input at the server 130 the medications the pharmacist intended to add to the automated dispensing machine 170, (3) go to the location of the automated dispensing machine 170 and login to the automated dispensing machine 170, (4) input into the automated dispensing machine 170 that the medications have been added, and (5) wait for the automated dispensing machine 170 to provide confirmation from the server 130 that the medications have been added.

The listing of actions can be customized (e.g., by adding or removing actions) by an administrator of the automated dispensing machine 170. For example, an action (not illustrated) can be added that permits the pharmacist or another authorized mobile client user to view medications ordered for a specific medical device 170, where the order or medication is in queue, and view a doctor's order(s) (e.g., by displaying a scanned copy) indicating a need for the medications. The pharmacist can further be provided with the option on the smartphone 110 to approve any such pending orders for medications.

The process 300 returns to decision step 313 to wait for another request to query an automated dispensing machine 170. The pharmacist using a touch input double presses the users button 414, with the first press to exit out of the actions interface 441, and the second press to activate an active users interface for the automated dispensing machines 170 to which the pharmacist has access. The application 222 determines that a request to perform an action on an automated dispensing machine 170 has been received, and the request is sent by the application 222 to the server 130 in step 314. In step 315 the request to perform an action on an automated dispensing machine 170 is received from the smartphone 110, and an appropriate instruction requesting a listing of active users (e.g., authorized medical device users and authorized mobile client users) for the automated dispensing machines 170 to which the pharmacist has access is sent to the corresponding automated dispensing machines 170 in step 316. In step 317, the automated dispensing machines 170 provide information on their respective active users (or, alternatively, the information is retrieved directly from the medical device tracking database 234 in the memory 232 of the server), and in step 318 the server 130 provides information on the active users to the application 222 for display on the pharmacist's smartphone 110.

The smartphone in step 319 displays a listing 444 of active users for the automated dispensing machines 170 to which the pharmacist has access as provided in the example active users interface 442 of FIG. 4E. The active users can include both authorized mobile device users, such as nurses, and authorized mobile client users, such as pharmacists and system administrators. The pharmacist can select any user in the list 444 by pressing on the user's actual name or user identification. The process 300 returns to decision step 313 to wait for another request to query an automated dispensing machine 170. The pharmacist using a touch input selects user JDOE 443, who the pharmacist knows as being a nurse. The application 222 determines in step 313 that a request to perform an action on an automated dispensing machine 170 has been received, and the request is sent by the application 222 to the server 130 in step 314. In step 315 the request to perform the action is received from the smartphone 110, and an appropriate instruction requesting information on nurse JDOE is sent to the medical device tracking database 234 in step 316. In step 317, the medical device tracking database 234 provides information on nurse JDOE, and in step 318 the server 130 provides information on JDOE to the application 222 for display on the pharmacist's smartphone 110.

The smartphone in step 319 displays information on nurse JDOE as provided in the example user detail interface 446 of FIG. 4F. The displayed information for nurse JDOE includes: a user identification 447, full name 448, time of last authorized login 449 to a mobile client 110, server 130, or medical device 170, a time when the user access will expire 450, whether the user may use bio-identification to access an application 222, server 130, or medical device 170, and an option to reset the user's password 452. The pharmacist can select any item in the user detail interface 446 to change that information for nurse JDOE.

Figure 4H:
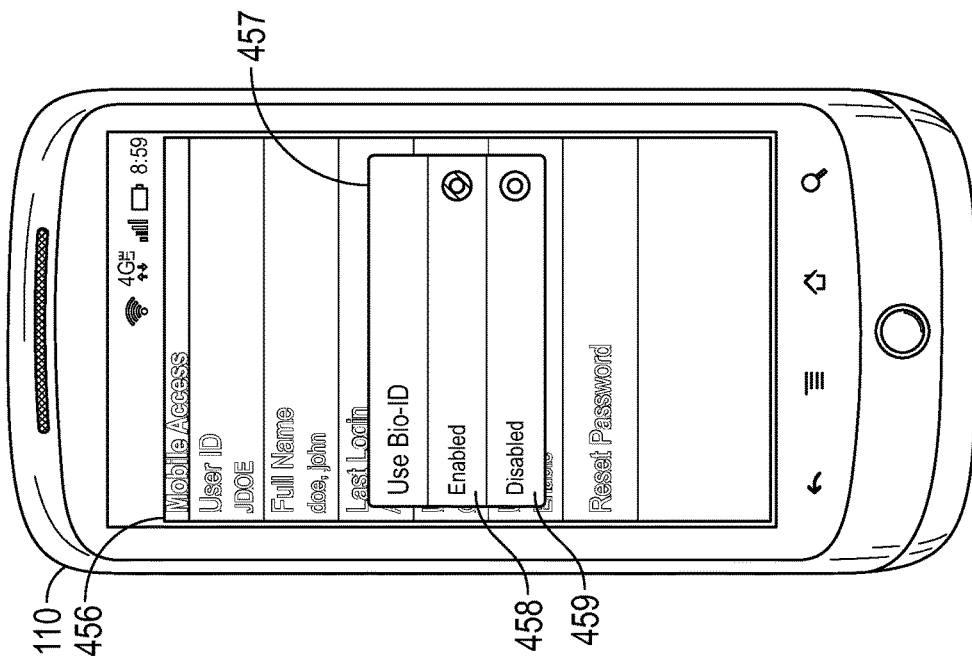
Figure 4G:
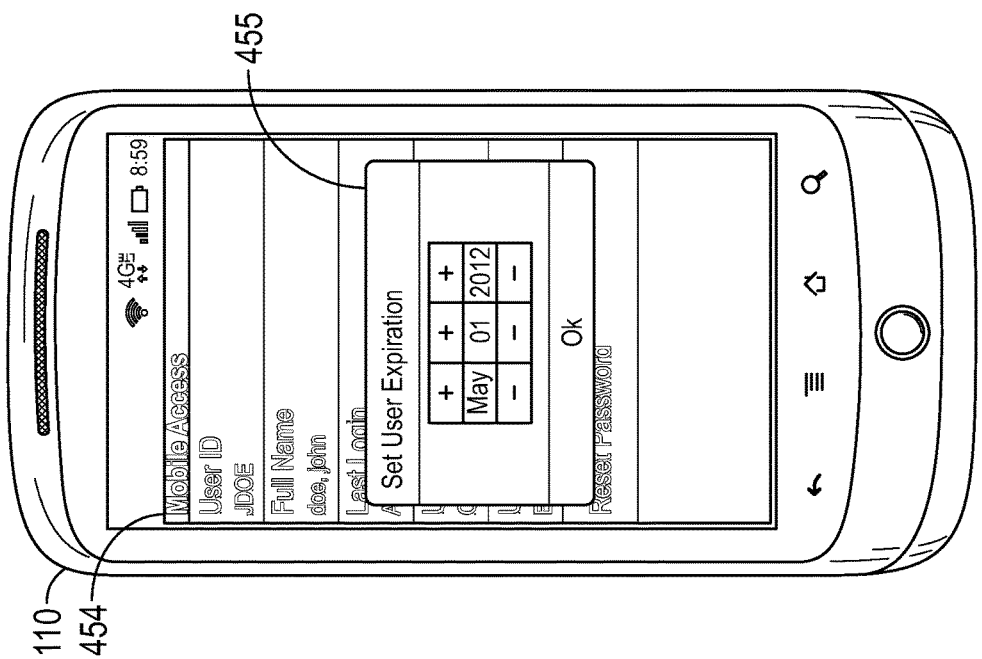

For example, the pharmacist can touch the user expiration detail 450 in the example user detail interface 446, and a prompt to set the nurse JDOE's access expiration date will be displayed as provided in the example illustration of a user expiration date interface 454 of FIG. 4G. The user expiration date interface 424 includes a prompt 455 permitting the pharmacist to adjust the nurse JDOE'S access expiration date. As another example, the pharmacist can touch the user bio-identification setting 451 in the example user detail interface 446, and a prompt to set whether the nurse JDOE can authenticate to an application 222 on a mobile client 110, a server 130, or a medical device 170 using bio-identification will be displayed as provided in the example illustration of a user bio-identification interface 456 of FIG. 4H. The user bio-identification interface 457 includes a prompt 455 that permits the pharmacist to either enable bio-identification authentication 458 for nurse JDOE, or disable bio-identification authentication 459 for nurse JDOE. As a further example, the pharmacist can touch the user password reset setting 452 in the example user detail interface 446, and a prompt to reset the password for nurse JDOE will be displayed as provided in the example illustration of a user password interface 460 of FIG. 4I. The user password interface 460 includes a prompt 461 that permits the pharmacist to enter a new password for nurse JDOE.

The process 300 returns to decision step 313 to wait for another request to query an automated dispensing machine 170. The pharmacist using a touch input presses the devices button 415 to activate an active devices interface for the automated dispensing machines 170 to which the pharmacist has access. The application 222 determines in step 313 that a request to perform an action on an automated dispensing machine 170 has been received, and the request is sent by the application 222 to the server 130 in step 314. In step 315 the request to perform an action on an automated dispensing machine 170 is received from the smartphone 110, and an appropriate instruction requesting a current status of automated dispensing machines 170 to which the pharmacist has access is sent to the corresponding automated dispensing machines 170 in step 316. In step 317, the automated dispensing machines 170 provide information on their respective status (or, alternatively, the information is retrieved directly from the medical device tracking database 234 in the memory 232 of the server), and in step 318 the server 130 provides information on the current status of the automated dispensing machines 170 to the application 222 for display on the pharmacist's smartphone 110.

The smartphone in step 319 displays a listing 463 of active automated dispensing machines 170 to which the pharmacist has access as provided in the example device listing interface 462 of FIG. 4J. The device listing interface 462 provides a name and location of each automated dispensing machine to which the pharmacist has access. For example, the automated dispensing machine named PAS35002 464 is located in the anesthesia department. In certain aspects, the medical devices 170 provided in the listing 463 can be sorted based on a proximity of the medical devices 170 to the user. The proximity can be determined or otherwise estimated, for example, using a GPS sensor 224 in the smartphone 110 and the known location of each of the medical devices 170. The pharmacist can select any medical device 170 in the list 463 of the device listing interface 462 by pressing on the medical device's name.

The process 300 returns to decision step 313 to wait for another request to query an automated dispensing machine 170. The pharmacist using a touch input selects automated dispensing machine PAS35002 464. The application 222 determines that a request to perform an action on an automated dispensing machine 170 has been received, and the request is sent by the application 222 to the server 130 in step 314. In step 315 the request to perform the action is received from the smartphone 110, and an appropriate instruction requesting information on the automated dispensing machine PAS35002 464 is sent to the automated dispensing machine PAS35002 464 in step 316. In step 317, the automated dispensing machine PAS35002 464 provides information on itself 464 to the server 130, and in step 318 the server 130 provides the information on the automated dispensing machine PAS35002 464 to the application 222 for display on the pharmacist's smartphone 110.

Figure 4L:
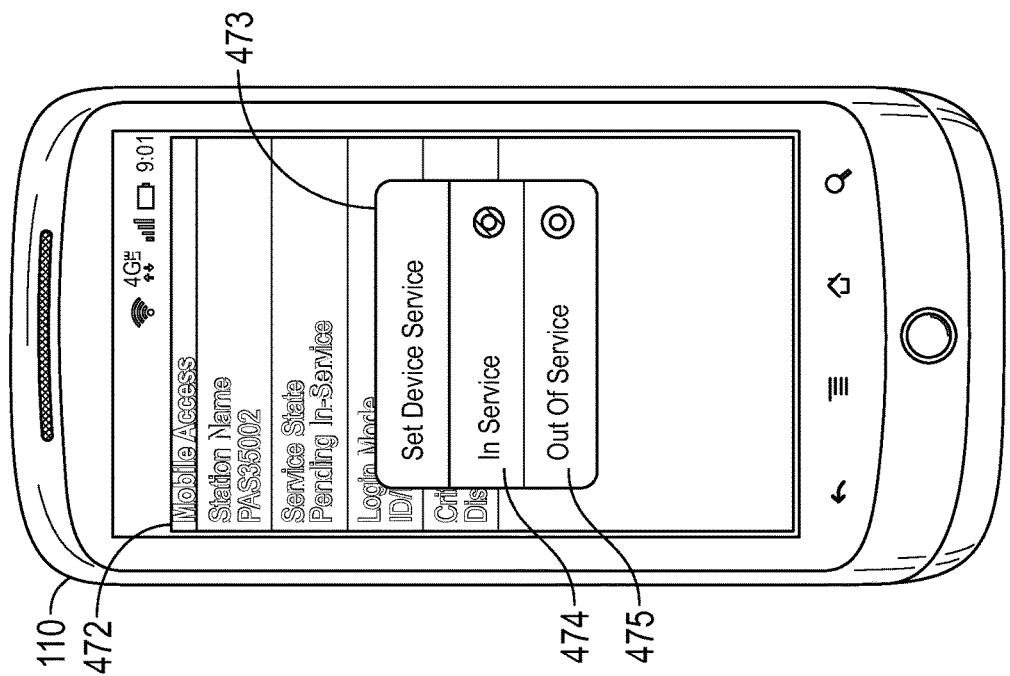
Figure 4K:
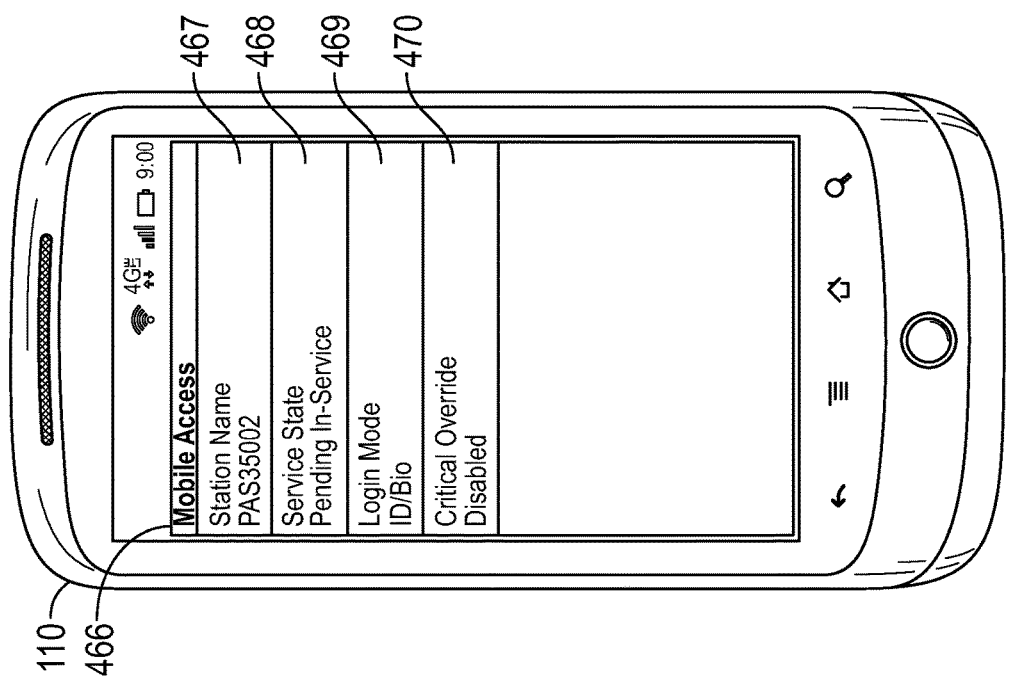

The smartphone in step 319 displays information on automated dispensing machine PAS35002 464 as provided in the example device detail interface 466 of FIG. 4K. The displayed information for automated dispensing machine PAS35002 464 includes: station name 467, service state 468, login process information 469, and critical override status 470. The pharmacist can select any item in the device detail interface 466 to change that information for automated dispensing machine PAS35002 464.

Figure 4N:
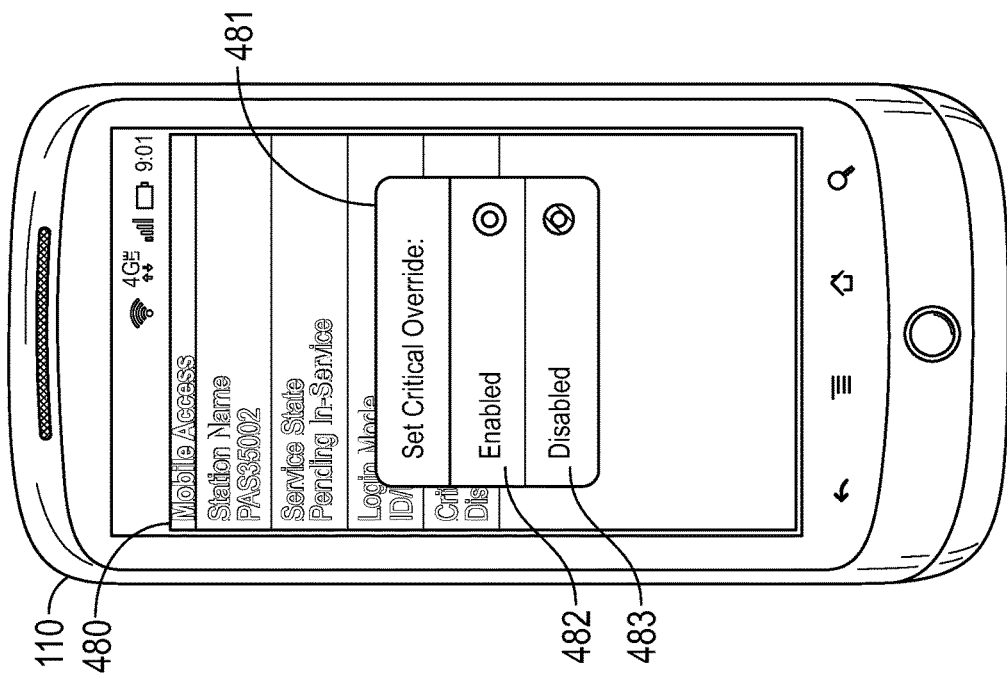
Figure 4M:
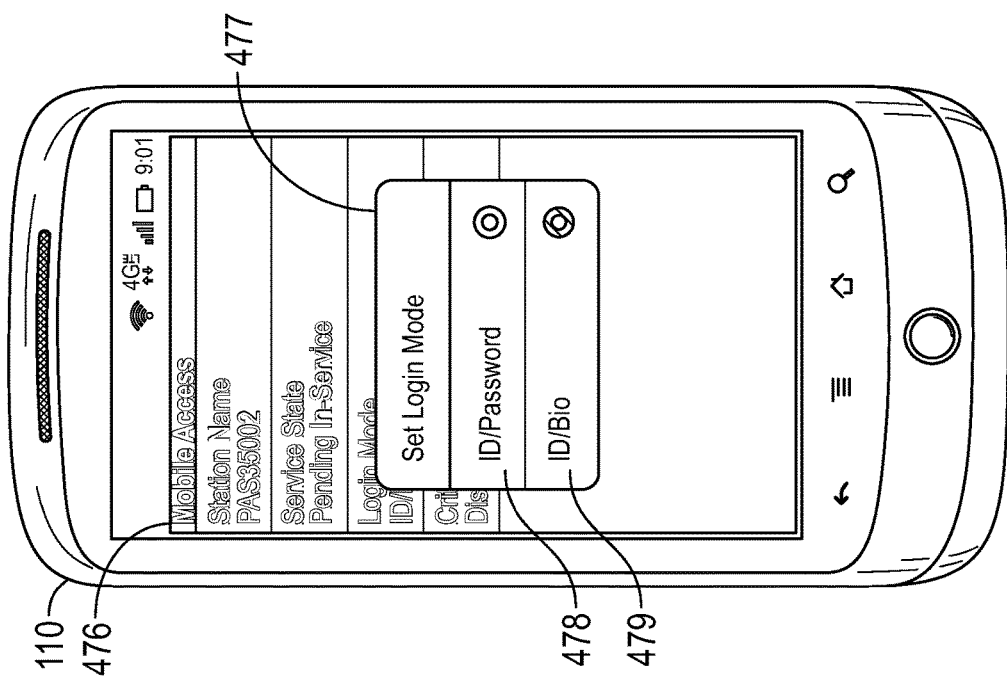

For example, the pharmacist can touch the service state 468 in the example device detail interface 466, and a prompt to set the service state for automated dispensing machine PAS35002 464 will be displayed as provided in the example illustration of a device service state interface 472 of FIG. 4L. The device service state interface 472 includes a prompt 473 permitting the pharmacist to change the service state automated dispensing machine PAS35002 464 from a current state of in service 474 to a new state of out of service 475. As another example, the pharmacist can touch the login process information 469 in the example device detail interface 466, and a prompt to set whether a password or bio-identification is required to access the automated dispensing machine PAS35002 464 is displayed as provided in the example illustration of a login mode interface 476 of FIG. 4M. The login mode interface 476 includes a prompt 477 that permits the pharmacist to either enable password identification authentication 478 for users of the automated dispensing machine PAS35002 464, or alternatively enable bio-identification authentication 479 for users of the automated dispensing machine PAS35002 464. As a further example, the pharmacist can touch the critical override status 470 in the example device detail interface 466, and a prompt 481 for setting the critical override status of the automated dispensing machine PAS35002 464 will be displayed as provided in the example illustration of a critical override interface 480 of FIG. 4N. The critical override interface 480 includes a prompt 481 that permits the pharmacist to enter enable 482 or disable 483 critical override for the automated dispensing machine PAS35002 464.

The process 300 returns to decision step 313 to wait for another request to query an automated dispensing machine 170. A request to query an automated dispensing machine 170 is not received by the application 222 from the pharmacist on the smartphone 110 within five minutes in decision step 313, so the process 300 proceeds to step 318 in which the application 222 on the smartphone 110 is de-authorized. The process 300 then ends in step 323.

Figure 5:
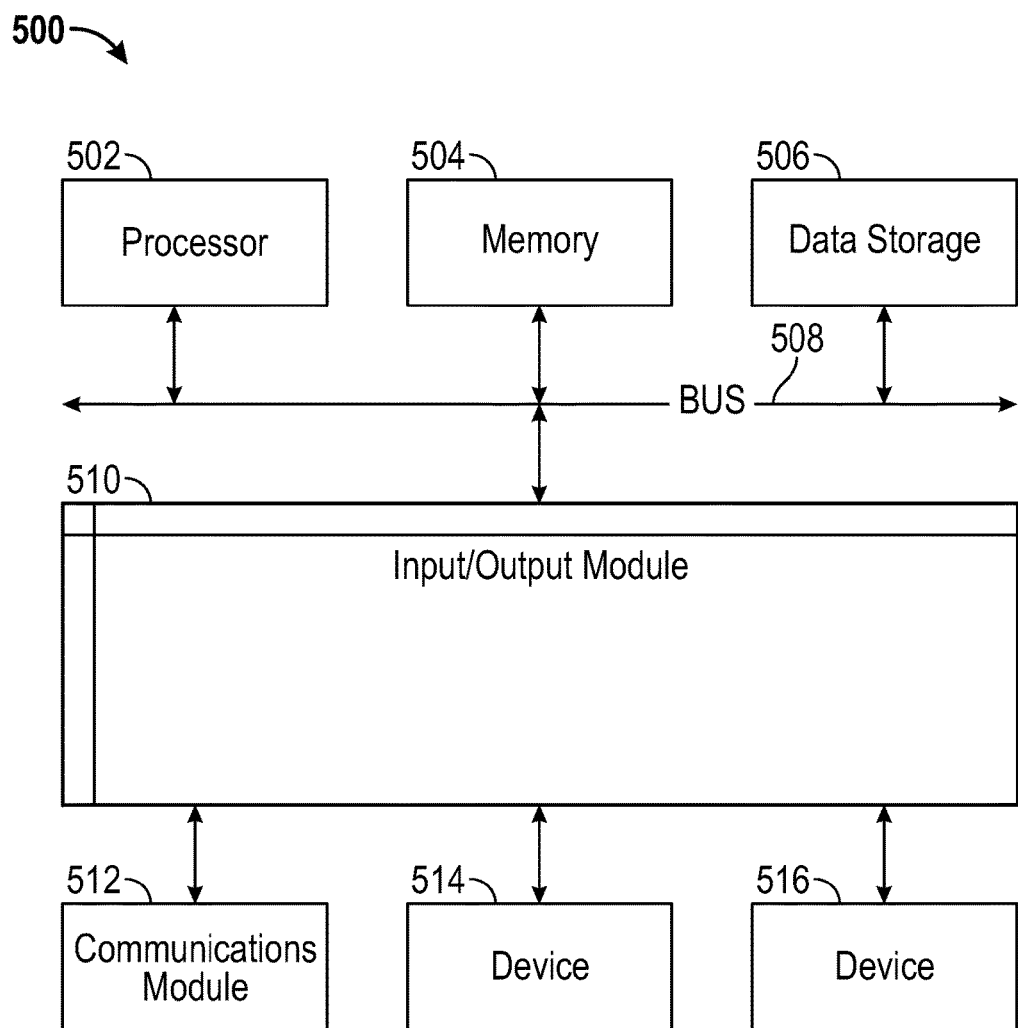
FIG. 5 is a block diagram illustrating an example computer system with which the client and server of FIG. 2 can be implemented.

FIG. 5 is a block diagram illustrating an example computer system 500 with which the mobile client 110 and server 130 of FIGS. 1 and 2 can be implemented. In certain aspects, the computer system 500 may be implemented using hardware or a combination of software and hardware, either in a dedicated server, or integrated into another entity, or distributed across multiple entities.

Computer system 500 (e.g., mobile client 110 and server 130) includes a bus 508 or other communication mechanism for communicating information, and a processor 502 (e.g., processor 212 and 236) coupled with bus 508 for processing information. By way of example, the computer system 500 may be implemented with one or more processors 502.

Processor 502 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information.

Computer system 500 can include, in addition to hardware, code that creates an execution environment for the computer program in question, e.g., code that constitutes processor firmware, a protocol stack, a database management system, an operating system, or a combination of one or more of them stored in an included memory 504 (e.g., memory 220 and 232), such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 508 for storing information and instructions to be executed by processor 502. The processor 502 and the memory 504 can be supplemented by, or incorporated in, special purpose logic circuitry.

The instructions may be stored in the memory 504 and implemented in one or more computer program products, i.e., one or more modules of computer program instructions encoded on a computer readable medium for execution by, or to control the operation of, the computer system 500, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, embeddable languages, and xml-based languages. Memory 504 may also be used for storing temporary variable or other intermediate information during execution of instructions to be executed by processor 502.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 500 further includes a data storage device 506 such as a magnetic disk or optical disk, coupled to bus 508 for storing information and instructions. Computer system 500 may be coupled via input/output module 510 to various devices 514 and 516. The input/output module 510 can be any input/output module. Example input/output modules 510 include data ports such as USB ports. The input/output module 510 is configured to connect to a communications module 512. Example communications modules 512 (e.g., communications modules 218 and 238) include networking interface cards, such as Ethernet cards and modems. In certain aspects, the input/output module 510 is configured to connect to a plurality of devices, such as an input device 514 (e.g., input devices 216 and 240) and/or an output device 516 (e.g., output devices 214 and 242). Example input devices 514 include a keyboard and a pointing device, e.g., a mouse or a trackball, by which a user can provide input to the computer system 500. Other kinds of input devices 514 can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Example output devices 516 include display devices, such as a LED (light emitting diode), CRT (cathode ray tube), or LCD (liquid crystal display) screen, for displaying information to the user.

According to one aspect of the present disclosure, the mobile client 110 and server 130 can be implemented using a computer system 500 in response to processor 502 executing one or more sequences of one or more instructions contained in memory 504. Such instructions may be read into memory 504 from another machine-readable medium, such as data storage device 506. Execution of the sequences of instructions contained in main memory 504 causes processor 502 to perform the process steps described herein. One or more processors in a multi-processing arrangement may also be employed to execute the sequences of instructions contained in memory 504. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. The communication network (e.g., network 150) can include, for example, any one or more of a PAN, LAN, CAN, MAN, WAN, BBN, the Internet, and the like. Further, the communication network can include, but is not limited to, for example, any one or more of the following network topologies, including a bus network, a star network, a ring network, a mesh network, a star-bus network, tree or hierarchical network, or the like. The communications modules 512 can be, for example, modems or Ethernet cards.

Computing system 500 can include clients and servers. A client and server are generally remote from each other and typically interact through a communication network. The relationship of client and server arises by virtue of computer programs running on the respective computers and having a client-server relationship to each other. Computer system 500 can be, for example, and without limitation, a desktop computer, laptop computer, or tablet computer. Computer system 500 can also be embedded in another device where appropriate, for example, and without limitation, a mobile telephone, a PDA, a mobile audio player, a GPS receiver, a video game console, and/or a television set top box.

The term "machine-readable storage medium" or "computer readable medium" as used herein refers to any medium or media that participates in providing instructions or data to processor 502 for execution. Such a medium may take many forms, including, but not limited to, non-volatile media, volatile media, and non-transitory transmission media. Non-volatile media include, for example, optical disks, magnetic disks, or flash memory, such as data storage device 506. Volatile media include dynamic memory, such as memory 504. Transmission media include coaxial cables, copper wire, and fiber optics, including the wires that comprise bus 508. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter effecting a machine-readable propagated signal, or a combination of one or more of them.

Systems, methods, and machine-readable media for controlling access to a medical device from a software application on a mobile device have been described. Using a mobile device, a user can be authenticated as an authorized mobile client user having access privileges to access and/or configure a medical device. Upon authorization, the user can access and configure the medical device over a network using an interface of the software application on the user's mobile device. For example, the user can change a profile of the medical device, change an authorization process of the medical device, disable or enable the medical device, and obtain current status information of the medical device. In certain aspects, the authorized user's ability to access and configure the medical device using the mobile device can be restricted based on the location of the mobile device vis-à-vis the medical device.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The subject matter of this specification has been described in terms of particular aspects, but other aspects can be implemented and are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other variations are within the scope of the following claims.

These and other implementations are within the scope of the following claims.

What is claimed is:

1. A system for controlling a medical device using a software application on a mobile device, the system comprising:
a memory comprising instructions; a processor configured to execute the instructions to:

receive, at a server and from a first user of a software application on a mobile device, a first user request for at least one of controlling access to a medical device by a second user, configuring the medical device, or a status of the medical device, wherein the first user request comprises a geolocation information of the first user, wherein the first user and the second user are different users;
determine, based on the geolocation information of the first user, whether the first user is authorized to control access to the medical device by the second user:
send an instruction from the server to the medical device based on the first user request; and
provide to the software application on the mobile device for display a result of the instruction, wherein the processor is configured to receive, in the first user request for controlling the second users access to the medical device when the geolocation information of the first user is acceptable, each one of:
a request for configuring one of a second user identification, a second user password, or an activation status in a second user's account, and
a request for modifying one of an existing second user password or an authorization process in the second user's account, wherein the second user's account is selected from a currently authorized user list for the medical device.

2. The system of claim 1, wherein the processor is further configured to execute the instructions to:
receive at the server and from the medical device an outcome of the instruction,
wherein the result of the instruction comprises information on the outcome of the instruction.

3. The system of claim 2, wherein the memory further comprises a database for tracking the medical device, and wherein the processor is further configured to execute the instructions to update the database based on at least one of the request received from the mobile device or the outcome of the request received from the medical device.

4. The system of claim 1, wherein the request from the software application on the mobile device is to query multiple medical devices, wherein at least two of the medical devices are located in different geographical locations.

5. The system of claim 1, wherein the medical device comprises a dispensing machine, respirator, or an infusion device.

6. The system of claim 1, wherein the mobile device comprises a smartphone or tablet computer, and wherein the software application is specific to usage on the mobile device.

7. The system of claim 1, wherein the processor is further configured to execute the instructions to:
receive a request from the software application on the mobile device for authorization to instruct the medical device and comprising a user identification data;
determine whether to authorize the software application on the mobile device based on the user identification data; and
send an authorization outcome to the software application on the mobile device when the user identification data indicates the software application is authorized on the mobile device.

8. The system of claim 1, wherein to determine whether the first user is authorized to control access by the second user to the medical device comprises determining, based on the geolocation information, a proximity of a mobile device location to a location of the medical device or to a location of the server.

9. The system of claim 1, wherein the request for the status of the medical device comprises a request for notifications specific to the medical device.

10. The system of claim 1, wherein the status of the medical device comprises information indicative of an inventory of the medical device, or information indicative of an infusion status of the medical device.

11. The system of claim 1, wherein the request for configuring the medical device comprises a request to change information indicative of an inventory of the medical device, or to change information indicative of an infusion configuration of the medical device.

12. The system of claim 11, wherein the request to change the information indicative of an inventory of the medical device comprises a confirmation that a medical item has been added or removed from the medical device.

13. The system of claim 1, further comprising configuring the server to establish communication between the first user on the mobile device and a second user handling the second user's account.

14. The system of claim 1, wherein the first user request for configuring the medical device comprises at least one of a request for a name of the medical device, a request for a location of the medical device, a request to configure an authorization process for the medical device, or a request to configure an availability of the medical device.

15. The system of claim 1, wherein the processor is further configured to execute the instructions to:
receive a request from the software application on the mobile device to open a communications channel for at least one of audio communication or text-based communication;
open the communications channel; and
send information on the communications channel to the software application on the mobile device.

16. A method for controlling a medical device using a software application on a mobile device, the method comprising:
receiving, at a server and from a first user of a software application on a mobile device, a first user request for at least one of controlling access to a medical device by a second user, configuring the medical device, or a status of the medical device, wherein the first user request comprises geolocation information of the first user, wherein the first user and the second user are different users;
determining, based on the geolocation information of the first user, whether the first user is authorized to control access to the medical device by the second user:
sending from the server an instruction to the medical device based on the first user request; and
providing to the software application on the mobile device for display a result of the instruction, wherein, when the geolocation information of the first user is acceptable:
receiving a first user request for controlling the second users access to the medical device comprises configuring, by the first user from the mobile device, one of a second user identification, a second user password, or an activation status in a second user's account, and a first user request for modifying one of an existing second user password or an authorization process in the second user's account, the second user's account selected from a currently authorized user list for the medical device.

17. The method of claim 16, further comprising:
receiving at the server and from the medical device an outcome of the instruction,
wherein the result of the instruction comprises information on the outcome of the instruction.

18. The method of claim 17, further comprising:
updating a database for tracking the medical device based on at least one of the first user request received from the mobile device or the outcome of a request received from the medical device.

19. The method of claim 16, wherein the first user request includes a query to multiple medical devices, wherein at least two of the medical devices are located in different geographical locations.

20. The method of claim 16, wherein the medical device comprises a dispensing machine, respirator, or an infusion device.

21. The method of claim 16, wherein the mobile device comprises a smartphone or tablet computer, and wherein the software application is specific to usage on the mobile device.

22. The method of claim 16, further comprising:
receiving a request from the software application on the mobile device for authorization to instruct the medical device and comprising user identification data;
determining whether to authorize the software application on the mobile device based on a first user identification data; and
sending an authorization outcome to the software application on the mobile device based on the determination.

23. The method of claim 16, wherein the first user request for authorization further comprises mobile device location data, and wherein the determination of whether to authorize the software application on the mobile device is further based on a proximity of a mobile device location to a location of the medical device or a location of the server.

24. The method of claim 16, wherein the first user request for the status of the medical device comprises a request for notifications specific to the medical device.

25. The method of claim 24, wherein the status of the medical device comprises information indicative of an inventory of the medical device, or information indicative of an infusion status of the medical device.

26. The method of claim 16, wherein the first user request for configuring the medical device comprises a request to change information indicative of an inventory of the medical device, or to change information indicative of an infusion configuration of the medical device.

27. The method of claim 26, wherein the request to change the information indicative of an inventory of the medical device comprises a confirmation that a medical item has been added or removed from the medical device.

28. The method of claim 16, further comprising configuring the server to establish communication between the first user on the mobile device and a second user handling the second user's account.

29. The method of claim 16, wherein the first user request for configuring the medical device comprises at least one of a request for a name of the medical device, a request for a location of the medical device, a request to configure an authorization process for the medical device, or a request to configure an availability of the medical device.

30. The method of claim 16, further comprising:
receiving a request from the software application on the mobile device to open a communications channel for at least one of audio communication or text-based communication;
opening the communications channel; and
sending information on the communications channel to the software application on the mobile device.

31. A non-transitory computer readable storage medium comprising machine-readable instructions for causing a processor to execute a method for controlling a medical device using a software application on a mobile device, the method comprising:
receiving, at a server and from a first user of a software application on a mobile device, a first user request for at least one of controlling access to a medical device by a second user, configuring the medical device, a status of the medical device, or a request from a software application on a mobile device to query a medical device, wherein the first user request comprises geolocation information of the first user, wherein the first user and the second user are different users;
determining, based on the geolocation information of the first user, whether the first user is authorized to control access to the medical device by the second user:
sending from the server an instruction to the medical device based on the query; and
providing to the software application on the mobile device for display a result of the instruction, wherein when the geolocation information of the first user is acceptable: the first user request for controlling the second users access to the medical device comprises a request for configuring one of a second user identification, a second user password, or an activation status in a second user's account, and a request for modifying one of an existing second user password or an authorization process in the second user's account, the second user's account selected from a currently authorized user list for the medical device.

* * * * *